United States Patent [19]
Olmstead

[11] Patent Number: 6,092,906
[45] Date of Patent: Jul. 25, 2000

[54] PERSONAL/PRIVATE LIGHT SCREEN

[76] Inventor: Charles H. Olmstead, 18 Kinsley Rd., Acton, Mass. 01720

[21] Appl. No.: 09/060,589

[22] Filed: Apr. 15, 1998

[51] Int. Cl.[7] ....................................................... F21V 9/16
[52] U.S. Cl. ............................. 362/105; 362/103; 362/84; 600/27
[58] Field of Search ............................. 362/84, 103, 105, 362/106; 600/27; 602/2, 74; 607/88

[56] References Cited

U.S. PATENT DOCUMENTS

| | | | |
|---|---|---|---|
| 4,777,937 | 10/1988 | Rush | 600/27 |
| 4,858,609 | 8/1989 | Cole | 128/395 |
| 4,902,274 | 2/1990 | Gleeson, III | 600/27 |
| 5,047,006 | 9/1991 | Brandston | 600/21 |
| 5,259,830 | 11/1993 | Masuda | 600/27 |
| 5,447,528 | 9/1995 | Gerardo | 607/88 |
| 5,503,637 | 4/1996 | Kyricos | 607/88 |

*Primary Examiner*—Y. Quach

[57] ABSTRACT

A lightweight light screen (1) that emits a low-intensity, diffused light of uniform brightness from its interior surface. The light screen covers both of a user's (2) eyes (3) when worn, thereby preventing ambient light from entering the user's eyes. The wearer of the light screen can see only the emitted light. The nature of the emitted light in combination with isolation from ambient visual stimuli provide a restful and therapeutic environment for the wearer. The light screen has two apertures (11) with shades (14, 15) that can be used uncover the apertures. The apertures are positioned with respect to each eye such that when uncovered the wearer can read or perform other short-focal-distance tasks that require eyesight while obtaining benefits from the emitted light. The combined area of the apertures is less than 5% of the light emitting area of the light screen so the user can maintain his/her sense of isolation while performing tasks and continue to derive benefit from irradiation.

5 Claims, 3 Drawing Sheets

PERSONAL/PRIVATE LIGHT SCREEN

BACKGROUND OF THE INVENTION

1. Field of the Invention

This invention relates generally to light screen that is wrom like eyeglasses by the user. The light screen is an electroluminescent lamp and is configured to isolate the wearer from ambient light. The light screen has small apertures positioned vith respect to the wearer's eyes that permit the wearer to read or perform other short-viewing-distance tasks that require eyesight while simultaneously being irradiated with light emitted from the interior surface of the light screen. The user can adjust the position of the apertures and adjust the width of the apertures. The size of the aperture is small enough to maintain the wearer's sense of being isolated from ambient visual stimuli.

The light screen and electric power supply system are of a size and configuration to enable use of the invention in almost any location of the wearer's choosing.

2. Description of Prior Art

It has been posited that special light can be used as therapy for persons suffering from a variety of maladies such as depression, seasonal affected disorder, disruption of circadian rhythms, etc. Various intensities, colors, and time duration of illumination have been proposed. In fact, even irradiating parts of the human body other than eyes, such as the backs of knee joints, have been suggested as being beneficial. Exposure to special light also is believed to be an aid to meditating.

Some believe that concurrent ambient visual stimuli detracts from the benefits that can be derived from the intended visual stimulus.

Whatever the validity of these theories, many people believe they feel better during or after (or both) a session of exposure to special light Many businesses supply lighting products intended for therapeutic purposes, as an aid for meditation, and for relief of mental stress.

One such class of products is a fixture with a bank of light bulbs, usually florescent, with back-surface reflectors that direct light from the source to the user. The user assumes a position near the light fixture and in the light path that will irradiate the desired portion of their body, usually eyes. This mechanism is simple to operate. Another advantage is the user can perform tasks such as reading, writing, sewing, etc. that do not require movement out of the path of the light. A disadvantage is that these fixtures are not small enough to be portable while being used and they require a significant amount of electrical power to create light. Furthermore, this light is created by a thermolurinenescent process that radiates ultra-violet and infrared wavelengths as well as light in the visible range. Sustained exposure to infrared and ultra-violet rays can damage the eye. Also, if only the eyes are intended for irradiation, much of the light created by these devices is wasted on all surfaces other than the eyes upon which the light impinges. In addition, the light might be an unwelcome distraction to other persons in the vicinity of the user. Lastly, since the user's field of vision encompasses more than the light fixture, other, unwanted visual stimuli may be present that can distract the user or otherwise render therapy less effective than desired.

Another class of products consists of a visor that can be worn on the user's head. The visor is equipped with several small light bulbs positioned partially out of the user's field of vision. Some of the light from the bulbs irradiates the user's eyes. This mechanism, too, is simple to operate. In addition, it somewhat mitigates some of the disadvantages of the larger fixture described previously. The light bulbs are positioned closer to the user's eyes and, hence, require less power for the same degree of irradiation. The power requirement is low enough to be satisfied with dry-cell batteries as the source, which enables the user to move about while being irradiated. Since the amount of radiation with a visor device is designed to be less than with a larger fixture device, the amount of light that might disturb other persons in the vicinity of the user is correspondingly less. However, as with the fixture device, the visor device does not prevent possible distraction of unwanted ambient visual stimuli.

One solution, at least partially, to the disadvantages of prior art described above is invention in U.S. Pat. No. 4,858,609: Bright Light Mask. Ambient light is completely excluded by the mask. The mask has apertures for admitting high intensity light to the user's eyes. These apertures are designed for the single purpose of introducing light into the mask and, indeed, the mechanisms such as light bulbs, lenses, or fiber optic cables claimed for achieving insertion of light into the mask precludes use of the apertures for viewing objects outside the mask.

Another invention that excludes ambient visual stimuli is described in U.S. Pat. No. 5,047,006: Personal integrating sphere system. An integrating sphere has a reflecting surface that is literally a sphere. This invention requires the user's head to be located inside such a sphere. The only entrance for light into the sphere are those specified for the light that is injected into the sphere.

However, the diameter of an integrating sphere has to be somewhat larger than the diameter of a user's head for the sphere's reflecting surface to provide "a field of illumination of substantially uniform intensity". If the diameter of a sphere relative to a users head is too small, the user's head will absorb much of the injected light before it can be reflected into the user's eyes. In addition, the position of the user's head with respect to the points where light is inserted into the sphere is another factor that determine the degree of shadowing that occurs as light rays are reflected from the surface. Shadowing will create a field of illumination that is not uniform.

An integrating sphere system has several other limitations. The first is that the equipment must be stationary. The user cannot move while their head is inside the sphere. Also, the equipment is cumbersome; it cannot be used just anywhere. Another limitation is the user does not have an option to view any object other than the reflecting surface of the sphere.

Some forms of therapy or meditation entail reading verse or prose or religious scripture while in a relaxed mental state. The invention described herein is a light screen that irradiates the user with a uniform light to facilitate relaxation and eliminates the intrusion of unwanted visual stimuli to the user's eyes. The wearer has the option to uncover apertures in the light screen for purposes of reading to enhance their therapy or meditation. The small area of the apertures does not permit admission of unwanted light The apertures can be covered when the wearer does not want to view objects outside the light screen. Because the light screen is positioned very close to the user's eyes, the amount of light necessary to satisfy the user is significantly less than with the prior art described previously. Consequently, power requirements are significantly less such that the light screen can be operated with dry-cell batteries, if the user chooses to do so. Also, the opaque property of the light screen insures that light emitted by the light screen will not be seen by other persons in the vicinity of the user.

OBJECTS AND ADVANTAGES

It is an object of the invention to exclude ambient light from entering the wearer's eyes and to direct light emanating from the interior surface of the light screen into the wearer's eyes.

It is a furter object to permit the wearer to read or perform other short viewing-distance tasks while wearing the light screen.

It is a further object to utilize electroluminescence process rather than thermoluminescence (incandescence) process for creating light thereby eliminating possibility of ultra violet radiation and infrared radiation that can injure the user's eyes.

It is a ftrther object to enable the user to employ a dry cell battery as a supply of electric energy.

It is a further object that use of the invention not be noticeable to other persons in the vicinity of the user.

It is a ftrther object for the complete apparatus to be less expensive than other kinds of light therapy devices.

BRIEF DESCRIPTION OF DRAWINGS

For a fuller understanding of the nature and objects of the invention, reference should be made to the following detailed description, taken in connection with the accompanying drawings, in which.

Reference Numerals in Drawings

| | | | |
|---|---|---|---|
| 1 | Light Screen | 9 | Inverter |
| 2 | User's Head | 10 | Dry Cell Battery |
| 3 | User's Eye | 11 | Aperture |
| 4 | Frame | 12 | User's Field of View |
| 5 | Pliable Material at Peripheral Edge | 13 | Focus Plane |
| | | 14 | Shade, counterclockwise |
| 6 | Band | 15 | Shade, clockwise |
| 7 | Electrical Connection Point | 16 | Pivot |
| 8 | Two-wire bundle | 17 | Retaining Cap |

SUMMARY OF THE INVENTION

This invention relates to a light screen configured to cover the wearer's eyes such that the only light that enters the wearer's eyes is the light that emanates from the interior surface of the light screen. The light screen has small apertures positioned directly in the wearer's line of near-field vision to permit the user to read or perform similar tasks while being irradiated. The user can cover the apertures when total isolation is desired.

The material of the light screen creates light by an electroluminescent process. Power input requirements are low. The light emitted by the light screen is of constant brightness, and contains no infrared or ultra-violet rays.

DESCRIPTION OF THE PREFERRED EMBODIMENT

Figure 1:
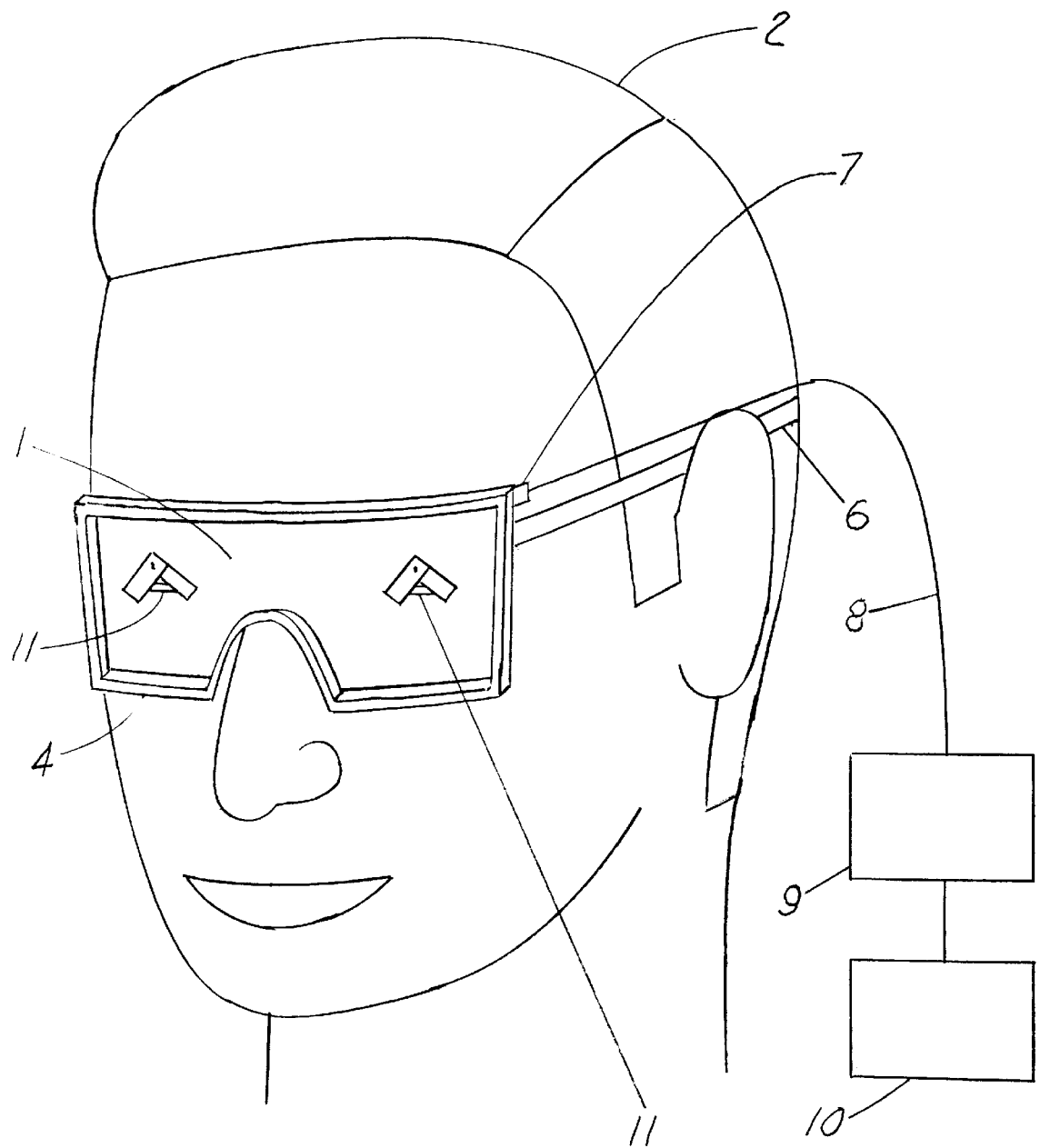
FIG. 1 is a front view depiction of a wearer's head showing the light screen positioned over the wearer's eyes. The frame contours the light screen to fit snugly against the wearer's face.
Figure 3:
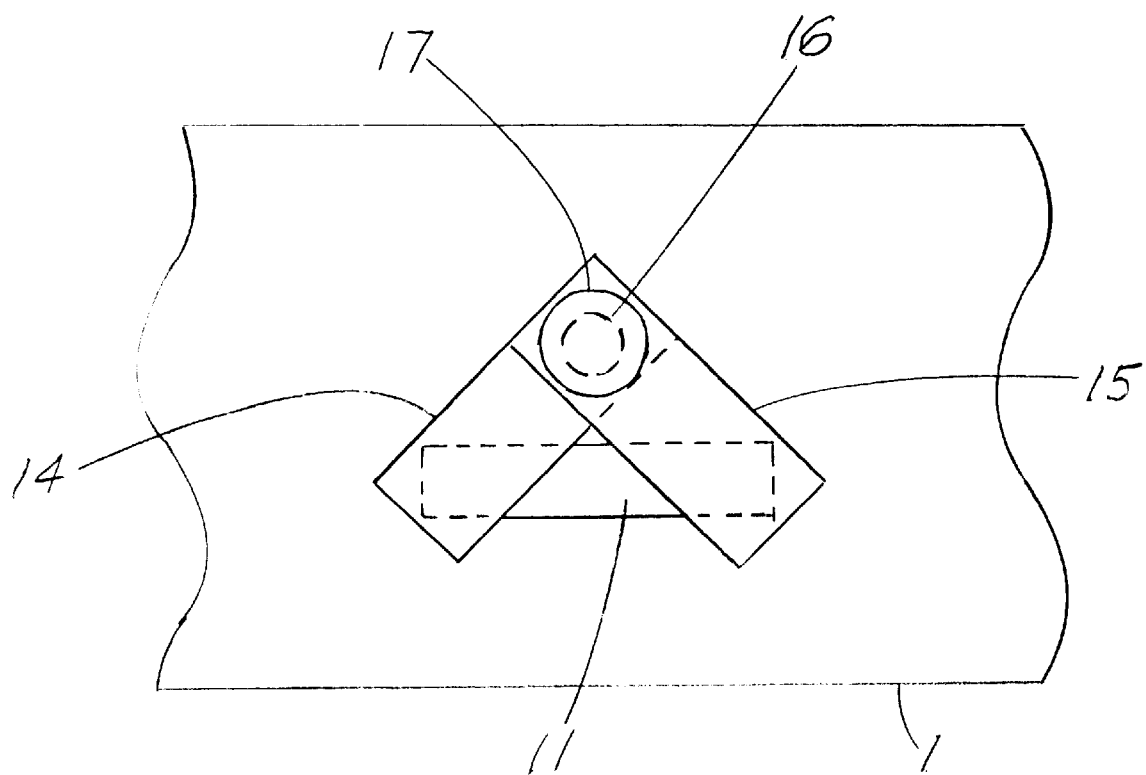
FIG. 3 is a detailed view of an aperture with two movable shades for adjusting the width of an aperture and the position of an aperture with respect to the second aperture.

In this embodiment, FIG. 1 shows light screen 1, which is a composite of several laminations of flexible plastic sheets with a total thickness of 0.015" or less. The area of light screenl is approximately 15 $in^2$, which is of sufficient size to cover the wearer's 2 eyes 3. Frame 4 causes light screen 1 to be formed into a generally cylindrical shape, the axis of the cylinder being more or less parallel to the axis of the wearer's 2 head. FIG. 3 shows pliable material 5 attached to the peripheral edge of light screen 1. The pliable material will deform to fill in gaps between the wearer's face and the peripheral edge of light screen. Frame 4 gently presses the pliable material 5 against the nose, cheeks, and forehead of the wearer 2. Very little pressure is required to insure that every part of the outer edge perimeter of light screenl is likely to be in contact with the wearer's 2 face. In this way ambient light is excluded from the wearer's eyes 3. Frame 4 can be made of a malleable material, permitting the wearer to bend it to fit the curvature of their face. Band 6 is fastened to the left and right edges of frame 4 and passes circumferentially around wearer's head. The band can be elastic.

Alternatively, frame 4 can be rigid. Exclusion of ambient visual stimuli while wearing a rigid frame is achieved by utilizing pliable material 5 that is slightly thicker than what is required with a malleable frame.

Light screen 1 is an electroluminescent lamp that emits light with constant brightness over the interior surface when a sufficient voltage of sufficient cycles per second is applied. The brightness of the lamp is proportional to both magnitude and frequency of the voltage.

Electroluminescent lamps are typically constructed of a transparent top layer insulator, a transparent top layer conductor, a bottom conductor, and an opaque bottom insulator. Phosphorous is sandwiched between the top and bottom conductor layers. The phosphorus will illuminate when voltage applied to the terminals of the two conductors changes potential. The emitted light is diffused and of uniform brightness. The chemical composition of the phosphors used to generate the light is selected to provide the desired color of emitted light. Typically, a white light is preferred.

The top layer insulator of light screenl that is closest to the wearer 2 and, hence forms the interior surface of light screenl can also be a color filter to enhance the color of the light received by the wearer 2.

The method of manufacturing the light screen material enables approximately 95% of the area of light screen to emit light. The outer perimeter of light screen and the area with connection point 7 to the electric source is located do not emit light In the discussion that follows, the term interior surface refers to the surface of light screen 1 that is nearest to the wearer 2 and exterior surface refers to the surface that is farthest from the wearer. The insulating layer that is the exterior surface of light screen I is opaque. In effect, light is emitted from the interior surface of light screen 1 in one direction only. The light emitted by light screen 1 is not visible to other people in the vicinity of the wearer 2.

The small size of light screen 1 and frame 4 enables it to be used anywhere and its use does not create a distraction to others.

The manufacture of electroluminescent lamps is well known to those practiced in the art as witnessed by the fact that these lamps are manufactured many companies in the United States.

Two wires in wire bundle 8 connect the output of inverter 9 to light screen 1 by means of connector point 7. Inverter 9 converts the DC voltage supplied by dry-cell battery 10 to an alternating current, AC, voltage. The AC voltage output of inverter 9 energizes the phosphor in light screen 1 to create light. The voltage and alternating frequency of voltage are selected to produce the desired intensity of emitted light Typical values are 120 volts and 500 cycles per second.

The manufacture of inverters is well known to those practiced in the art as witnessed by the numerous companies in the United States that supply these devices.

Figure 2:
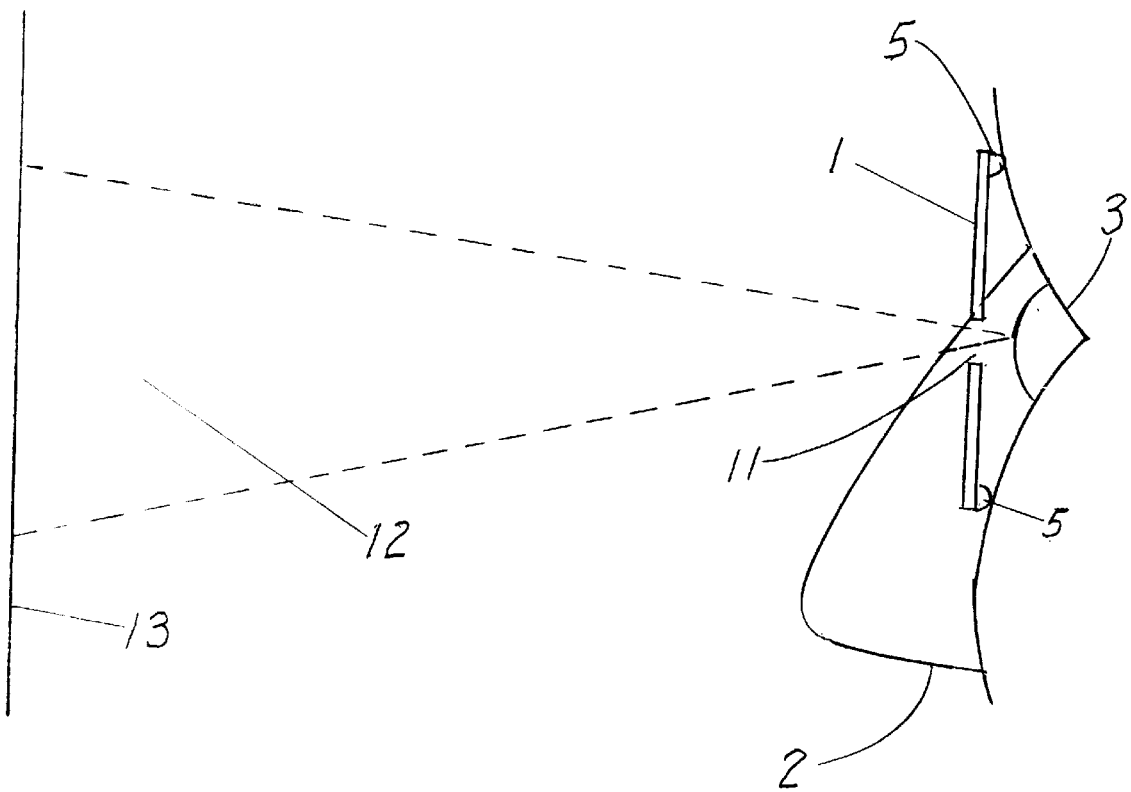
FIG. 2 is a cross sectional view of a light screen in contact with a wearer's brow and cheek and of a wearer's eye and depicting the field of view of a wearer's eye through an aperture in the light screen.

FIG. 2 shows a sectional view of light screen 1 with an aperture 11 that provides a field of view 12 for viewing objects located a short distance beyond light screen 1. The apertures preferably are slits of the same dimensions in all of the laminations of the light screen. The aperture can be holes or transparent areas. A slit is the preferred configuration for the aperture because it facilitates adjustment to the width of the aperture and determining the position of the aperture with respect to the wearer's nose.

FIG. 2 shows a sectional view of aperture 11. There is one aperture for each eye 3. The aperture 11 is positioned close to the wearer's eye 3. Two small apertures, each less than 0.125" in height and less than 0.125" in width, enable the wearer 2 to focus both eyes on a plane 13 located a short distance from the exterior surface of light screen 1. The total area of two such apertures 11 relative to the area of the interior surface of light screen 1 is miniscule, less than 1% of the total area. Apertures in the light screen permit the wearer to perform a limited number of tasks (that do not include ambulatory movement) while maintaining a sense of total immersion in the light of their choice with no visual distractions from objects in their vicinity or from events occurring around them. The apertures can be covered when the user does not want to view objects beyond the light screen.

FIG. 3 is a detailed view of means to adjust the width of the aperture 11 and to adjust the position of one aperture with respect to the second aperture. Shades 14 and 15 rotate about rivet-like pivot 16. For purposes of discussion, shade 14 is designated shade for counterclockwise rotation and shade 15 is designated shade for clockwise rotation. The retaining cap 17 of pivot 16 provides a snug fit for the shades such that friction retains each shade, 14 and 15, in the position the wearer has put it. As shade 15 is rotated clockwise and shade 14 is rotated counterclockwise, the width of aperture 11 is diminished.

Also, the position of the aperture with respect to the second aperture can be adjusted by the relative rotation of the two shades 14 and 15.

Conclusions, Ramifications, and Scope

Accordingly, the reader will see that the personal/private light screen can be used purposes of light therapy or mediation. All ambient visual stimuli are excluded from the user's eyes. The electroluminescent material produces a uniform whithe light that is completely eye-safe in that no ultra violet or infra red light is emitted. Electric power requirements are modest; the light screen can be operated with a small dry cell battery. The light screen is approximately the same size and weight as conventional eyeglasses. Light from the light screen is not visible to anybody other than the wearer. Thus, the light screen can be wsed readily and inconspicuously wherever and whenever the user chooses to do so. The user has the option to use apertures to read or perform other tasks while wearing the light mask. The area of the apertures is small enough relative to the light emitting area of the light screen so that the user will continue to maintain a sense of isolation for ambient visual stimuli.

It will be seen that the objects set forth above, and those made apparent from the foregoing description are effectively attained and since certain changes may be made in the above construction and without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of scope of the invention which, as a matter of language, might be said to fall therebetween.

Now that the invention has been described,

What I claim is:

1. A light screen having a light emitting area fits over a wearer's eyes, said light emitting area emitting light, said light emitting area having two apertures positioned in the lines of vision of the wearer, and each of the apertures having a viewing area defined by a width and height of the aperture.

2. A light screen as recited in claim 1 in which said lght screen is a flexible material.

3. A light screen as recited in claim 1 with cover means covering said apertures.

4. A light screen as recited in claim 3 with means to position said covers to adjust said widths of the said apertures and to adjust positions of the said lines of vision.

5. A light screen as recited in claim 1 where each of said viewing areas of each of said two apertures is less than one twentieth of said light emitting area of the said light screen.

* * * * *